(12) United States Patent
Rodriguez

(10) Patent No.: US 10,603,630 B2
(45) Date of Patent: Mar. 31, 2020

(54) MICROWAVE OVEN DEODORANT DEVICE

(71) Applicant: Eric Rodriguez, Kissimmee, FL (US)

(72) Inventor: Eric Rodriguez, Kissimmee, FL (US)

( * ) Notice: Subject to any disclaimer, the term of this patent is extended or adjusted under 35 U.S.C. 154(b) by 254 days.

(21) Appl. No.: 15/668,188

(22) Filed: Aug. 3, 2017

(65) Prior Publication Data

US 2019/0039018 A1 Feb. 7, 2019

(51) Int. Cl.
*B01D 53/38* (2006.01)
*B65D 81/26* (2006.01)
*A61L 9/16* (2006.01)
*A61L 2/12* (2006.01)
*A61L 9/013* (2006.01)
*A61L 9/03* (2006.01)
*A61L 9/014* (2006.01)

(52) U.S. Cl.
CPC .............. *B01D 53/38* (2013.01); *A61L 2/12* (2013.01); *A61L 9/013* (2013.01); *A61L 9/014* (2013.01); *A61L 9/037* (2013.01); *A61L 9/16* (2013.01); *B65D 81/266* (2013.01); *A61L 2209/13* (2013.01); *B01D 2257/90* (2013.01); *B01D 2258/0275* (2013.01)

(58) Field of Classification Search
CPC ............ B01D 53/38; B01D 2258/0275; B01D 2257/90; A61L 2/12; A61L 9/013; A61L 9/014; A61L 9/037; A61L 9/16; A61L 2209/13; B65D 81/266
USPC ....... 219/678, 679, 756, 725, 757, 734, 735; 422/120, 121, 305, 307; 239/44, 13; 607/114
See application file for complete search history.

(56) References Cited

U.S. PATENT DOCUMENTS

| 1,742,962 | A | * | 1/1930 | McCrosky | A24F 25/02 239/55 |
| 4,219,573 | A | * | 8/1980 | Borek | A47J 36/022 219/727 |
| 4,873,101 | A | * | 10/1989 | Larson | A23L 3/01 426/113 |
| 5,007,529 | A | * | 4/1991 | Spector | A61L 9/03 206/0.5 |
| 5,096,722 | A | * | 3/1992 | Bair | B65D 81/264 426/107 |
| 5,178,839 | A | * | 1/1993 | Spector | A61L 9/03 206/472 |
| D378,126 | S | * | 2/1997 | Williams | D23/366 |
| 5,733,271 | A | * | 3/1998 | Bjørn | A61F 5/441 604/333 |
| 5,993,480 | A | * | 11/1999 | Burrows | A61F 7/02 607/112 |

(Continued)

FOREIGN PATENT DOCUMENTS

WO WO 8909068 10/1989

*Primary Examiner* — Jimmy Chou
(74) *Attorney, Agent, or Firm* — Jason T. Daniel, Esq.; Daniel Law Offices, P.A.

(57) ABSTRACT

A microwave oven deodorant device includes a microwave safe bag having an interior space, and a plurality of apertures. An absorbent member is positioned within the interior space and is coated with a liquid based scented fragrance. A cover is removably positioned onto the bag so as to cover each of the apertures to create an airtight environment within the bag. Upon removal of the cover, and receiving heat from an oven, the scented material produces steam that escapes through the apertures.

6 Claims, 4 Drawing Sheets

(56) References Cited

U.S. PATENT DOCUMENTS

| | | | |
|---|---|---|---|
| 6,444,963 B1* | 9/2002 | Donahue | A61L 9/03 219/678 |
| 7,087,871 B2 | 8/2006 | Cherry | |
| 7,141,770 B2* | 11/2006 | Zafiroglu | B65D 81/3461 219/725 |
| 8,263,918 B2* | 9/2012 | Hach | B32B 27/32 219/725 |
| 8,648,030 B2* | 2/2014 | Groshek | B01D 53/04 512/4 |
| 9,988,200 B2* | 6/2018 | Cichowski | B65D 81/3453 |
| 2002/0113067 A1* | 8/2002 | Donahue | A61L 9/03 219/679 |
| 2003/0131439 A1* | 7/2003 | Wen | A47L 5/24 15/344 |
| 2004/0164074 A1* | 8/2004 | Newton | H05B 6/6408 219/734 |
| 2005/0011883 A1* | 1/2005 | Clothier | F28D 20/0056 219/618 |
| 2005/0184059 A1* | 8/2005 | Clothier | H05B 6/62 219/618 |
| 2006/0042467 A1* | 3/2006 | Maru | B01D 53/0407 96/134 |
| 2010/0180770 A1* | 7/2010 | Pagano | B01D 53/0415 96/108 |
| 2010/0189608 A1* | 7/2010 | Chan | B01D 53/0415 422/122 |
| 2010/0247372 A1* | 9/2010 | Pohl | A01M 1/2061 422/4 |
| 2011/0079658 A1* | 4/2011 | Santini | A61L 9/035 239/44 |
| 2012/0046720 A1* | 2/2012 | Ishizaki | A61F 7/02 607/114 |
| 2012/0273586 A1* | 11/2012 | Shook | A61L 9/042 239/13 |
| 2014/0346065 A1* | 11/2014 | Chijoff | A47J 39/00 206/233 |
| 2015/0196678 A1* | 7/2015 | Picken, Jr. | A61L 9/014 422/122 |
| 2015/0352241 A1* | 12/2015 | Furner | A61L 9/122 422/105 |
| 2016/0250370 A1* | 9/2016 | Orito | A61L 9/032 422/122 |
| 2018/0229914 A1* | 8/2018 | Bahrami | A45C 13/103 |

* cited by examiner

MICROWAVE OVEN DEODORANT DEVICE

TECHNICAL FIELD

The present invention relates generally to heat producing devices, and more particularly to a vaporization lighter.

BACKGROUND

The statements in this section merely provide background information related to the present disclosure and may not constitute prior art.

When using a microwave oven to cook or reheat items, it is not uncommon for strong odors to be created. Depending on the type of substance undergoing the cooking/reheating procedure, these odors may be a simple annoyance, or may be so pungent so as to cause severe discomfort for those nearby. In either instance, the odors are caused by the increased temperatures of the microwave which evaporates the liquids within the substance, causing the same to become airborne and to quickly spread.

Although there are many types of odor masking sprays currently available, each of these sprays are typically designed in aerosol form, and are designed to be sprayed around the room in which a microwave is located. In this regard, such devices simply replace the unpleasant odor in the room with a more powerful scent, but do nothing to eliminate the actual source of the odor inside the microwave. To this end, a user must physically clean the interior of the microwave using a towel and/or additional cleaning solutions. Failure to do so may cause the odor to linger and/or to be imported into subsequent items cooked by the microwave.

As such, it would be beneficial to provide a microwave deodorant device that can function to eliminate unpleasant odors from a microwave oven without suffering from the drawbacks described above.

SUMMARY OF THE INVENTION

The present invention is directed to a microwave oven deodorant device. One embodiment of the present invention can include a microwave safe bag having an interior space, and a plurality of apertures. An absorbent member such as a sponge, for example, can be positioned within the interior space and can be coated with any number of liquid based scented fragrances. In one embodiment, the device includes a cover that is removably positioned so as to cover each of the apertures to create an airtight environment within the bag. Upon removal of the cover, and receiving heat from an oven, the scented material produces steam that functions to mask unpleasant odors.

In another embodiment, the bag includes a releasable seam for replacing spent absorbent members with refill members.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

Figure 1:
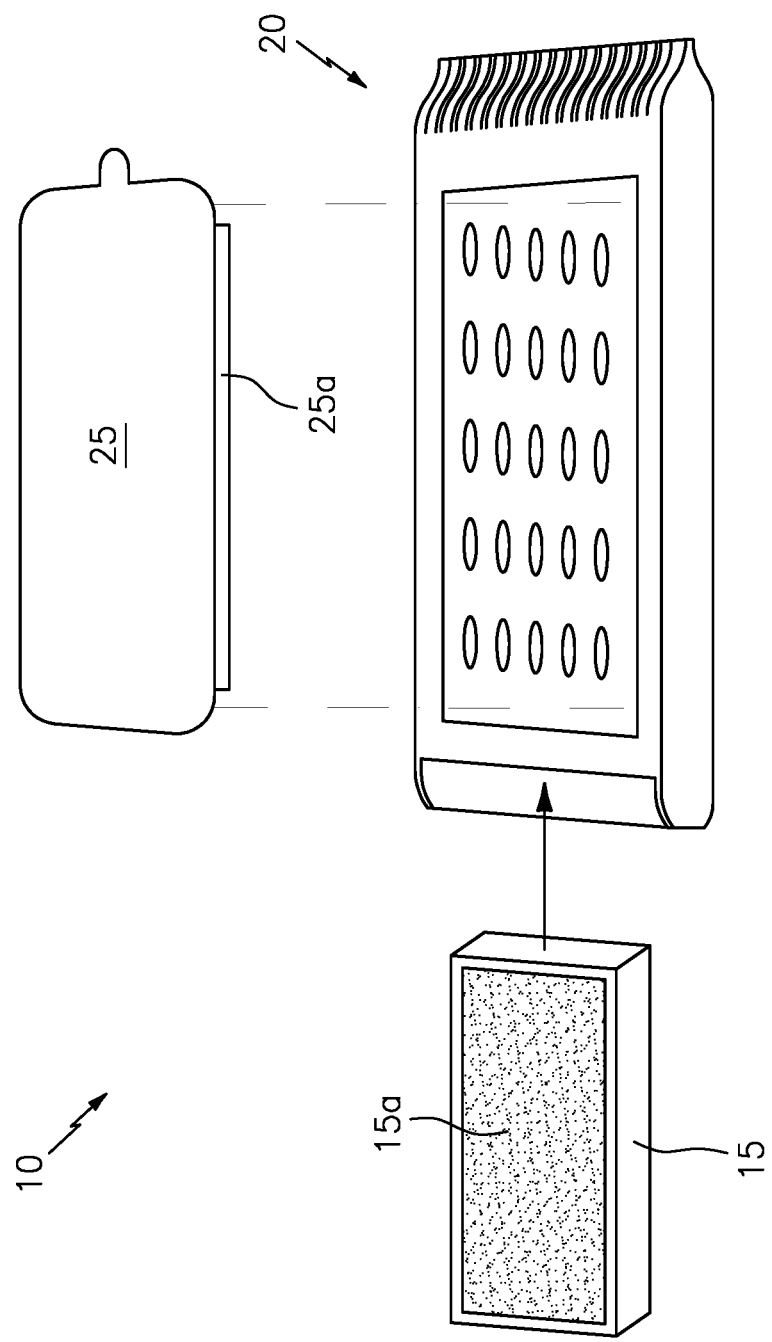
FIG. 1 is an exploded parts view of the microwave oven deodorant device that is useful for understanding the inventive concepts disclosed herein.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Although described for use with a microwave oven, this is for illustrative purposes only, as the below described device can be utilized with any number of different types of ovens so as to perform the inventive concepts disclosed herein.

As described herein, the term "removably secured," and derivatives thereof shall be used to describe a situation wherein two or more objects are joined together in a non-permanent manner so as to allow the same objects to be repeatedly joined and separated.

FIGS. 1-4 illustrate various embodiments of a microwave oven deodorant device 10 that are useful for understanding the inventive concepts disclosed herein. In each of the drawings, identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

FIG. 1 is an exploded parts view of the device components that can include, essentially, an absorbent member 15, a microwave safe bag 20, and a removable cover 25.

As described herein, the absorbent member 15 can include, comprise or consist of any number of different materials that are capable of absorbing and retaining fluids. In the preferred embodiment, the member 15 can comprise an environmentally friendly cellulose sponge, or other type of plant based material that is biodegradable and compostable. Of course, any number of other absorbent members such as cotton, foam and the like are also contemplated.

Prior to being packaged within the bag 20, the absorbent member can be coated/saturated with any number of scented fragrances 15a. In the preferred embodiment, the scented fragrances can be liquid based so as to evaporate and produce steam upon being heated to a temperature of around 212° F. Several nonlimiting examples of suitable scented fragrances include essential oils, lemon, orange and citrus liquids/extracts, for example.

Figure 2:
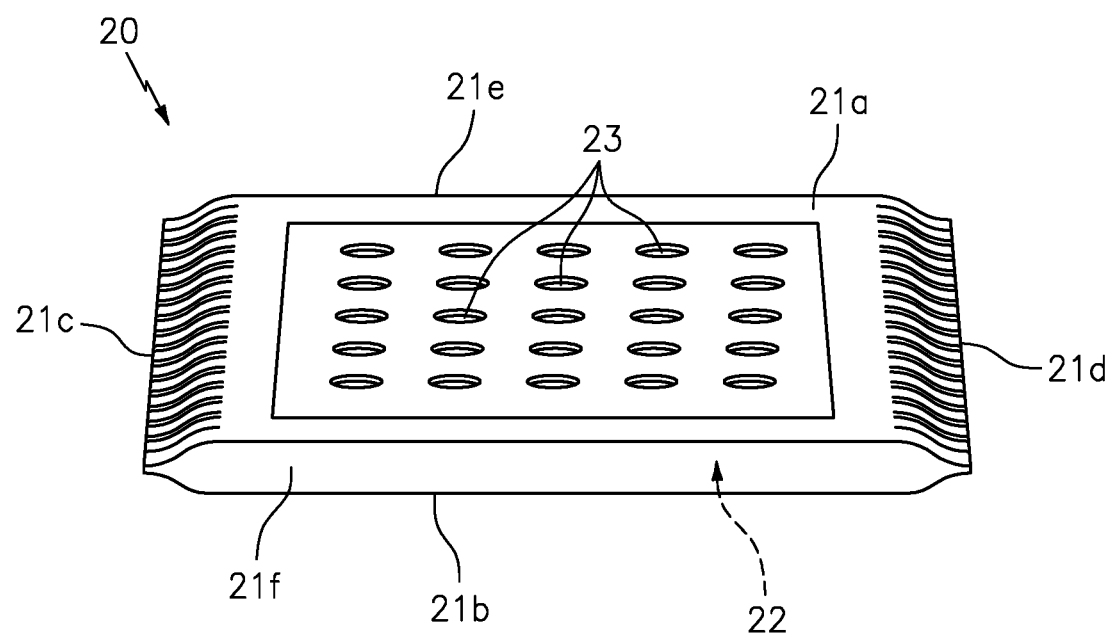
FIG. 2 is a perspective view of the bag portion of the microwave oven deodorant device, in accordance with one embodiment of the invention.

As shown in FIG. 2, one embodiment of the bag 20 can include a top surface 21a, a bottom surface 21b, and a plurality of side surfaces 21c-21f. The bag can be sealed along one or more of the side surfaces to form an interior space 22 into which the absorbent member 15 can be secured.

As described herein, the bag 20 can include any number of different shapes and sizes, and can be constructed from any number of different airtight materials that are suitable for exposure to high temperatures e.g., up to 400° F. without becoming damaged and/or releasing toxins (i.e., microwave safe). Several nonlimiting examples include heat-resistant nylon, polypropylene, and polyethylene, among others, for example.

As shown, the bag 20 can include a plurality of apertures 23 extending from the top surface 21a into the interior space 22. As will be described below, the apertures can function to allow the steam from the scented fragrances to escape the bag when heated by the oven.

Returning to FIG. 1, the removable cover 25 can preferably comprise a single piece of airtight material having a shape that is suitable for covering each of the apertures. The cover can include a connector 25a such as glue, for example, along the bottom surface and can be affixed to the top surface of the bag 21a. When so positioned, with the cover 25, the bag can maintain an airtight interior space that prevents the moisture within the absorbent member from evaporating prematurely.

In the preferred embodiment, the absorbent member 15 can be positioned within the bag 20 at a time of initial manufacture, and can be permanently sealed therein, so as to create a single-use product; however, other embodiments are also contemplated.

Figure 3:
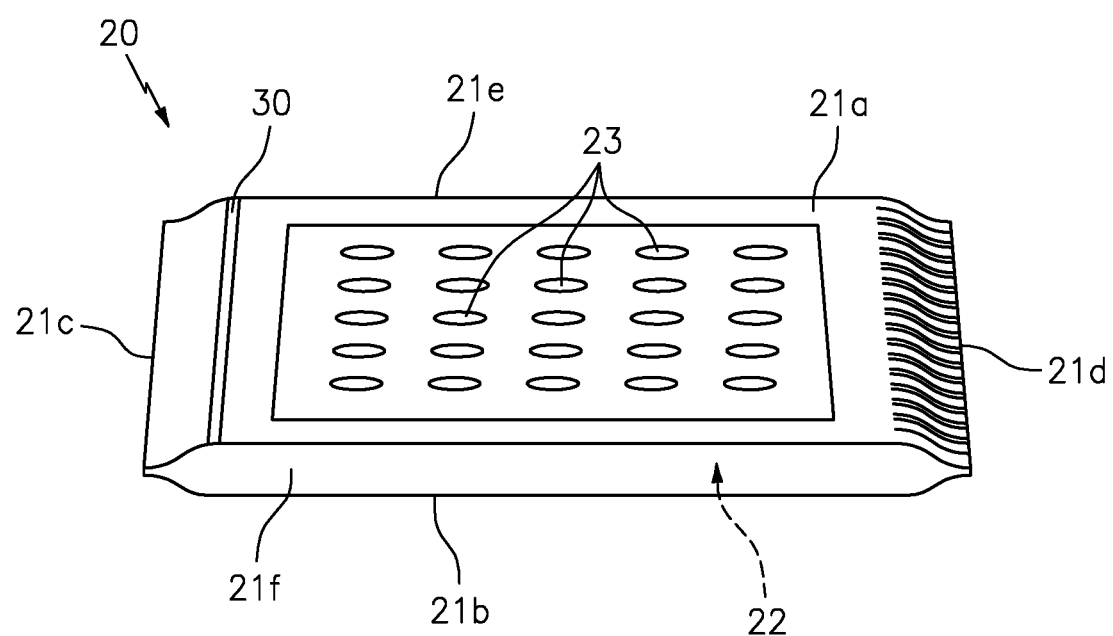
FIG. 3 is another perspective view of the bag portion of the microwave oven deodorant device, in accordance with one embodiment of the invention.

To this end, FIG. 3 illustrates one embodiment of the device 10 that includes a releasable seam 30, such as a zip seal or slider seal, for example, that can be positioned along one side of the bag 20. The seam 30 can function to allow a user to remove a used absorbent member 15 and replace the same with a fresh absorbent member that can be shipped and sold as a refill unit.

Figure 4:
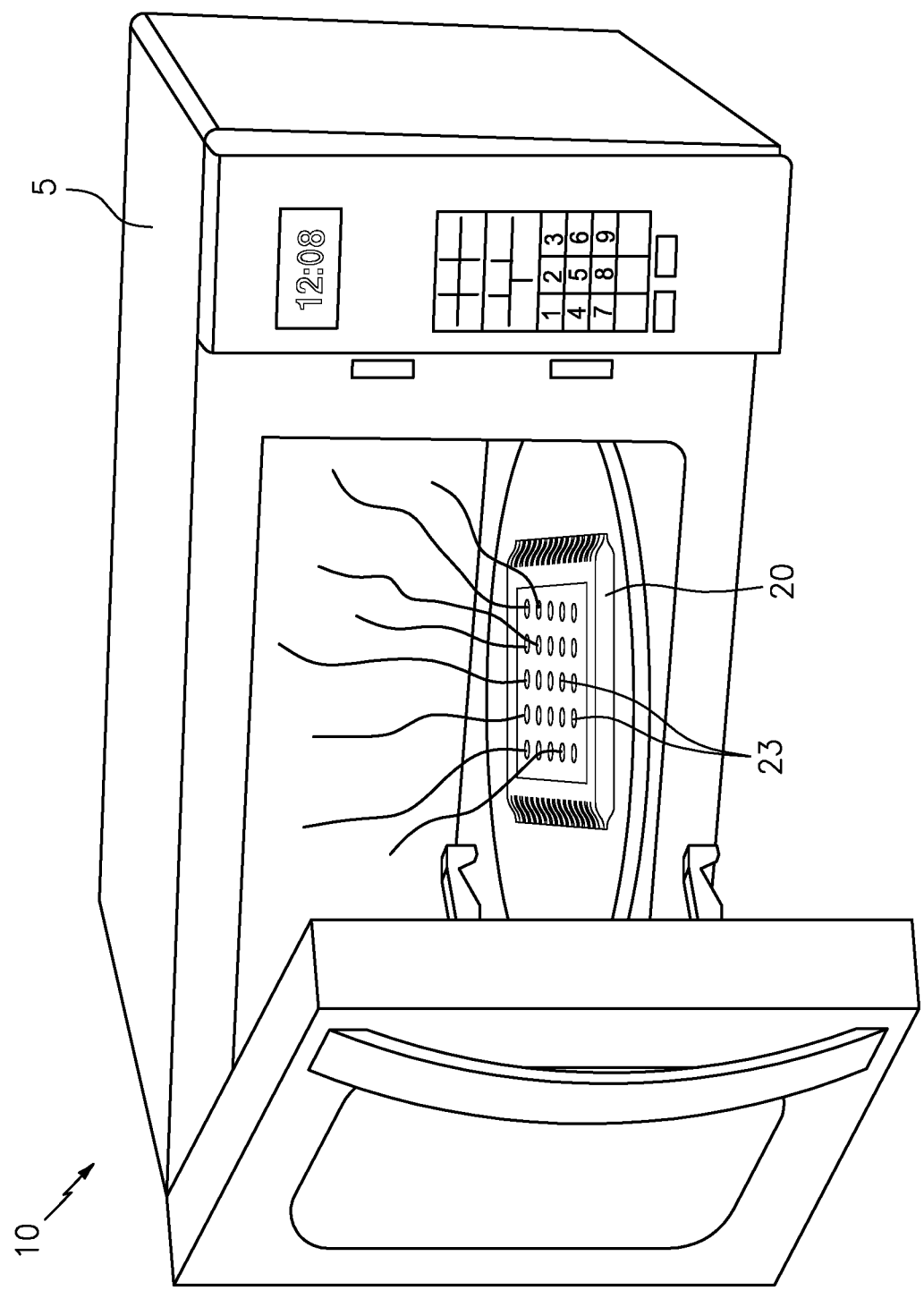
FIG. 4 is a perspective view of the microwave oven deodorant device in operation, in accordance with one embodiment of the invention.

FIG. 4 illustrates one embodiment of the device 10 in operation. As shown, the device 10 can be positioned within an oven 5, such as the illustrated microwave, for example, and the cover can be removed. The microwave can function to heat the device until the liquid within the absorbent member turns to steam S, and travels through the apertures 23. To this end, the steam functions to perform a cleaning action within the microwave that can cover and mask the odor of any food remnants still located therein. Moreover, when the door is opened, the steam will escape the microwave and provide a pleasant aroma that masks any unpleasant odors in the surrounding area.

Although the above embodiments have been described as including separate individual elements, the inventive concepts disclosed herein are not so limiting. To this end, one of skill in the art will recognize that one or more individually identified elements may be formed together as one or more continuous elements, either through manufacturing processes, such as welding, casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Likewise, the terms "consisting" shall be used to describe only those components identified. In each instance where a device comprises certain elements, it will inherently consist of each of those identified elements as well.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A deodorant device, comprising:
a microwave safe bag having an interior space, a top surface and a plurality of apertures extending from the top surface to the interior space;
an absorbent member that is positioned within the interior space;
a scented fragrance that is embedded within the absorbent member;
a cover that is removably secured along the top surface of the bag, said cover including a bottom surface that is configured to cover each of the plurality of apertures, wherein the cover comprises a connector to allow the cover to be affixed to the top surface of the bag; and
a releasable seam that is disposed along the microwave safe bag, and being configured to allow removal of the absorbent member from the bag.

2. The device of claim 1, wherein the scented fragrance is liquid based and is configured to produce steam that passes through the plurality of apertures when the device is heated by an oven.

3. The device of claim 1, wherein the scented fragrance comprises one or more essential oils.

4. The device of claim 1, wherein the absorbent member is permanently disposed within the interior space of the microwave safe bag.

5. The device of claim 1, wherein the absorbent member comprises a sponge.

6. The device of claim 1, wherein the connector is glue.

* * * * *